United States Patent [19]

Coates

[11] Patent Number: 4,885,301

[45] Date of Patent: Dec. 5, 1989

[54] PURINONE DERIVATIVES WHICH HAVE BRONCHODILATOR, VASODILATOR AND ANTI-ALLERGIC ACTIVITIES

[75] Inventor: William J. Coates, Welwyn Garden City, England

[73] Assignee: Smith Kline & French Laboratories Limited, Welwyn Garden City, England

[21] Appl. No.: 148,791

[22] Filed: Jan. 27, 1988

[30] Foreign Application Priority Data

Feb. 2, 1987 [GB] United Kingdom ............... 8702300
Feb. 2, 1987 [GB] United Kingdom ............... 8702301

[51] Int. Cl.$^4$ .................. A61K 31/52; C07D 471/30
[52] U.S. Cl. ............................ 514/263; 544/265; 548/337
[58] Field of Search ................... 544/265; 514/263

[56] References Cited

U.S. PATENT DOCUMENTS

| | | | |
|---|---|---|---|
| 3,437,661 | 4/1969 | Fuzimoto et al. | 544/265 |
| 3,819,631 | 6/1974 | Broughton et al. | 544/254 |
| 4,039,544 | 8/1977 | Broughton et al. | 544/254 |
| 4,460,590 | 7/1984 | Müller | 544/254 X |

FOREIGN PATENT DOCUMENTS 1545574 7/1969 Fed. Rep. of Germany.
1338235 11/1973 United Kingdom.

OTHER PUBLICATIONS

Bronghton, B. J. et al., J. Med. Chem., vol. 18, No. 11, 1117 (1975).
Fossard, N. et al., Br. J. Pharmac., vol. 73, 933–938 (1981).
Martin, W. et al., J. Pharmacol. Exp. Ther., vol. 237, No. 2, 539–547 (1986).
Lunt, E. Progress in Pharmaceutical Research, 4, 41–132 (1982).
Schroder, E. et al., "Arzneimittelschemie I", 1976, G. Thieme Verlag Stuttgart, West Germany, pp. 24–38, Chapter 7.1.
Chemical Abstracts, vol. 69, 10477z (1968), Fujimoto et al.
Chemical Abstracts, vol. 77, 10167t (1972), Otsuka et al.
Chemical Abstracts, vol. 101, 54988a (1984), Mokrushin et al.
Chemical Abstracts, vol. 97, 24147q (1982), Parkin et al.
World Patent 86/00305 of Cavender et al., published Jan. 16, 1986.
Patent Abstracts of Japan, vol. 6, No. 73, (C-101)(951) May 8, 1982.
Bergmann et al., Chemical Abstracts, vol. 59:5168e–f (1963).
Ohsaki et al., Chemical Abstracts, vol. 106:84536x (1987).
Casonline search report, p. 47, answer 34, "6H–Purin-6-One, 1,7–Dihydro-2-Phenyl", pp. 60–63, references for answer 34.

Primary Examiner—Mukund J. Shah
Assistant Examiner—Diana G. Rivers
Attorney, Agent, or Firm—Nancy S. Mayer; Janice E. Williams; Alan D. Lourie

[57] ABSTRACT

This invention relates to purinone derivatives which have bronchodilator, vasodilator and anti-allergic activities. A compound of the invention is 2-(2-propoxyphenyl)-6-purinone.

21 Claims, No Drawings

PURINONE DERIVATIVES WHICH HAVE BRONCHODILATOR, VASODILATOR AND ANTI-ALLERGIC ACTIVITIES

The present invention relates to purinone derivatives and in particular to such compounds having a substituted phenyl group at the 2-position of the purinone ring. This invention further relates to intermediates in their preparation, pharmaceutical compositions containing them and a method of effecting bronchodilatation or vasodilatation by administering them. The compounds of this invention are inhibitors of a calmodulin insensitive cyclic GMP phosphodiesterase and are of use in combatting such conditions wherein such inhibition is thought to be beneficial. The compounds of this invention are bronchodilators and are therefore of use in combatting chronic reversible obstructive lung diseases such as asthma and bronchitis. In addition the compounds of the present invention exhibit anti-allergic activity and are therefore of use in combatting allergic diseases such as allergic asthma, allergic rhinitis, urticaria and irritable bowel syndrome. Furthermore the compounds of this invention are vasodilators and are therefore of value in combatting angina, hypertension and congestive heart failure.

Accordingly the present invention provides compounds of the formula (1):

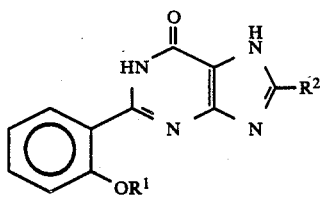

and pharmaceutically acceptable salts thereof, wherein
$R^1$ is $C_{1-6}$alkyl or $C_{2-6}$alkenyl, and
$R^2$ is hydrogen or hydroxy.

Suitably $R^1$ is $C_{2-5}$alkyl for example ethyl, n-propyl, isopropyl, butyl, isobutyl or pentyl.

Suitably $R^1$ is $C_{3-5}$alkenyl for example allyl, butenyl or pentenyl.

Preferably $R^1$ is n-propyl.

Suitably $R^2$ is hydrogen. Suitably $R^2$ is hydroxy.

Particular compounds of this invention are:
2-(2-propoxyphenyl)-6-purinone,
2-(2-ethoxyphenyl)-6-purinone,
2-(2-butoxyphenyl)-6-purinone,
2-(2-isobutoxyphenyl)-6-purinone,
2-(2-propoxyphenyl)purine-6,8-dione,
2-(2-methoxyphenyl)purine-6,8-dione,
2-(2-ethoxyphenyl)purine-6,8-dione,
2-(2-butoxyphenyl)purine-6,8-dione,
2-(2-isobutoxyphenyl)purine-6,8-dione, and
2-(2-allyloxyphenyl)purine-6-8-dione
and pharmaceutically acceptable salts thereof.

This invention covers all tautomeric forms of compounds of formula (1). For example the compound of the formula (1) wherein $R^2$ is hydroxy can exist in a tautomeric keto form:

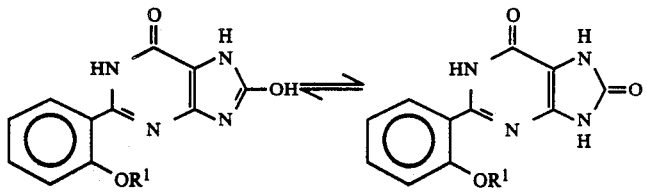

Compounds of the formula (1) wherein $R^2$ is hydrogen may form pharmaceutically acceptable salts with acids such as hydrochloric, hydrobromic, sulphuric, phosphoric, acetic, citric, maleic, lactic, ascorbic, fumaric, oxalic, methanesulphonic and ethanesulphonic acids.

Compounds of the formula (1) may form pharmaceutically acceptable salts with metal ions, such as alkali metals for example sodium and potassium, or with an ammonium ion.

In order to use a compound of the formula (1) or a pharmaceutically acceptable salt thereof for the treatment of humans and other mammals it is normally formulated in accordance with standard pharmaceutical practice as a pharmaceutical composition.

Compounds of formula (1) and their pharmaceutically acceptable salts may be administered in standard manner for the treatment of the indicated diseases, for example orally, parenterally, trans-dermally, rectally, via inhalation or via buccal administration.

Compounds of formula (1) and their pharmaceutically acceptable salts which are active when given orally or via buccal administration can be formulated as liquids, syrups, tablets, capsules and lozenges. An oral liquid formulation will generally consist of a suspension or solution of the compound or salt in a liquid carrier for example, ethanol, glycerine or water with a flavouring or colouring agent. Where the composition is in the form of a tablet, any pharmaceutical carrier routinely used for preparing solid formulations may be used. Examples of such carriers include magnesium stearate, starch, celluloses, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil, for example polyethylene glycol, polyvinylpyrrolidone, lecithin, arachis oil, or sesame oil.

A typical suppository formulation comprises a compound of formula (1) or a pharmaceutically acceptable salt thereof which is active when administered in this way, with a binding and/or lubricating agent, for example polymeric glycols, gelatins, cocoa-butter or other low melting vegetable waxes or fats.

Typical transdermal formulations comprise a conventional aqueous or non-aqueous vehicle, for example a cream, ointment, lotion or paste or are in the form of a medicated plaster, patch or membrane.

Typical compositions for inhalation are in the form of a solution, suspension or emulsion that may be administered in the form of an aerosol using a conventional propellant such as dichlorodifluoromethane or trichlorofluoromethane, or are in the form of a powder for insufflation.

Preferably the composition is in unit dosage form, for example a tablet, capsule or metered aerosol dose, so that the patient may administer to himself a single dose.

Each dosage unit for oral administration contains suitably from 0.001 mg/Kg to 3 mg/Kg, and preferably from 0.005 mg/Kg to 1.5 mg/Kg, and each dosage unit for parenteral administration contains suitably from 0.001 mg/Kg to 1 mg/Kg, of a compound of formula (1) or a pharmaceutically acceptable salt thereof calculated as the free base.

The daily dosage regimen for oral administration is suitably about 0.001 mg/Kg to 12 mg/Kg, of a compound of formula (1) or a pharmaceutically acceptable salt thereof calculated as the free base. The daily dosage regimen for parenteral administration is suitably about 0.001 mg/Kg to 4 mg/Kg, for example about 0.005 mg/Kg to 1 mg/Kg, of a compound of the formula (1) or a pharmaceutically acceptable salt thereof calculated as the free base. The active ingredient may be administered as required, for example from 1 to 8 times a day or by infusion. The compositions of the invention are bronchodilators and are useful in chronic reversible obstructive lung disease for example asthma and bronchitis. The compositions of the present invention have vasodilator activity and are of use in the treatment of angina, hypertension and congestive heart failure. Such conditions can be treated by administration orally, topically, rectally, parenterally or by inhalation. For administration by inhalation dosages are controlled by a valve, are administered as required and for an adult are conveniently in the range of 0.1–5.0 mg of a compound of the formula (1) or a pharmaceutically acceptable salt thereof.

The compounds of this invention may be co-administered with other pharmaceutically active compounds, for example in combination, concurrently or sequentially. Conveniently the compounds of this invention and the other active compound or compounds are formulated in a pharmaceutical composition. Examples of compounds which may be included in pharmaceutical compositions with the compounds of the formula (1) are bronchodilators such as sympathomimetic amines for example isoprenaline, isoetharine, salbutamol, phenylephrine and ephedrine or xanthine derivatives for example theophylline and aminophylline, anti-allergic agents for example disodium cromoglycate, histamine $H_1$-antagonists, vasodilators for example hydralazine, angiotensin converting enzyme inhibitors for example captopril, anti-anginal agents for example isosorbide nitrate, glyceryl trinitrate and pentaerythritol tetranitrate, anti-arrhythmic agents for example quinidine, procainamide and lignocaine, calcium antagonists for example verapamil and nifedipine, diuretics such as thiazides and related compounds for example bendrofluazide, chlorothiazide, chlorothalidone, hydrochlorothiazide, and other diuretics for example frusemide and triamterene, and sedatives for example nitrazepam, flurazepam and diazepam.

The compounds of the formula (1) or pharmaceutically acceptable salts thereof can be prepared by a process which comprises:

(a) for compounds wherein $R^2$ is hydrogen, reacting a compound of the formula (2):

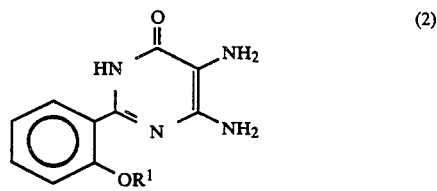

wherein $R^1$ is as hereinbefore defined, with a formylating agent;

(b) for compounds wherein $R^2$ is hydroxy, reacting a compound of the formula (2) as hereinbefore defined with a carbonylating agent;

(c) for compounds wherein $R^2$ is hydrogen, reacting a compound of the formula (3):

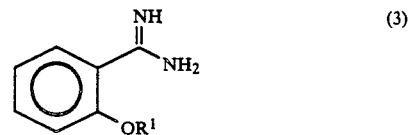

wherein $R^1$ is as hereinbefore defined with 4-amino-5-imidazolecarboxamide, (d) for compounds wherein $R^2$ is hydrogen, cyclising a compound of the formula (4):

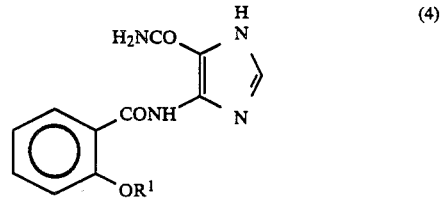

wherein $R^1$ is as hereinbefore defined;
and thereafter optionally forming a pharmaceutically acceptable salt.

The reaction between a compound of the formula (2) and a formylating agent is conveniently performed in the absence of a solvent or in the presence of a suitable solvent such as a $C_{1-4}$ alcohol, pyridine or N-methylpyrrolidone, at ambient or elevated temperature, for example 50°–250° C., preferably 100°–200° C. Examples of formylating agents include formic acid, $C_{1-4}$ alkyl formate, formamide, $C_{1-4}$ alkyl formamide, formamidine, $C_{1-4}$ alkyl formamidine or tri($C_{1-4}$)alkyl orthoformate. Suitable a compound of the formula (2) is reacted with formamidine acetate in the presence of sodium acetate. Preferably the compound of the formula (2) is used in the form of an acid addition salt, for example the sulphate, and is reacted with an excess of a formylating agent, for example formamide.

The reaction between a compound of the formula (2) and a carbonylating agent is conveniently performed in the absence of a solvent or in a suitable solvent such as a halohydrocarbon, pyridine or toluene, at ambient or elevated temperature, for example 50°–250° C. Suitable carbonylating agents include urea, di($C_{1-4}$)alkylcarbonate, $C_{1-4}$alkyl chloroformate, phosgene, trichloromethyl chloroformate or carbonyldiimidazole.

Suitably a compound of the formula (3) is reacted with an acid addition salt of 4-amino-5-imidazolecarboxamide, for example the hydrochloride, in the absence of a solvent or in a suitable solvent such as a $C_{1-4}$alcohol, pyridine or N-methylpyrrolidone at an elevated temperature, for example 50°–250° C.

Suitably a compound of the formula (4) is cyclised by heating at an elevated temperature, for example 50°–150° C., in the presence of an acid or a base in a suitable solvent such as aqueous $C_{1-4}$alcohols, water, toluene, a halohydrocarbon or acetonitrile.

A compound of the formula (4) can be prepared by reaction of 4-amino-5-imidazolecarboxamide with a compound of the formula (5):

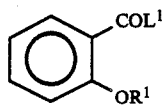

(5)

wherein $L^1$ is halo and $R^1$ is as hereinbefore defined.

Suitable $L^1$ is chloro or bromo. Suitably a compound of the formula (5) is reacted with 4-amino-5-imidazolecarboxamide at ambient or elevated temperature e.g. 50°–100° C. in a suitable solvent such as toluene, acetonitrile or a halohydrocarbon e.g. chloroform or dichloromethane, optionally in the presence of a base such as pyridine or triethylamine, to form a compound of the formula (4) which may be cyclised in situ to form a compound of the formula (1) wherein $R^2$ is hydrogen or may be isolated and thereafter cyclised as hereinbefore described.

Compounds of the formulae (2) and (3) are known or preparable in conventional manner from U.S. Pat. No. 3,819,631 herein incorporated by reference.

Pharmaceutically acceptable acid addition salts of the compounds of the formula (1) wherein $R^2$ is hydrogen may be prepared from the corresponding base of the compounds of the formula (1) in conventional manner. For example the base may be reacted with an acid in a $C_{1-4}$alkanol, or an ion-exchange resin may be used. The salts of the compounds of the formula (1) may be interconverted using ion-exchange resins. Non-pharmaceutically acceptable salts are therefore of use as they can be converted to pharmaceutically acceptable salts.

Pharmaceutically acceptable base addition salts of the compounds of the formula (1) may be prepared by standard methods, for example by reacting a solution of the compound of the formula (1) with a solution of the base.

The following biological test methods, data and Examples serve to illustrate this invention.

Bronchodilatation—In vivo

Male guinea-pigs of the Dunkin Hartley strain (500–600 g) were anaesthetised with Sagatal (pentobarbital sodium) (60 mg/kg). Airway resistance was measured using a modification of the classical Konzett-Rossler technique (Versuchsanordnung zu Untersuchungen an der Bronchialmuskulatur. Naunyn-Schmiedebergs Arch. Exp. Path. Pharmak., vol 195: pp 71–74, (1940). U46619 (9,11-methanoepoxy-PGH$_2$) was infused i.v. at a rate of 2.5 nmol/min, this produced a steady state of bronchoconstriction (approximately 120% increase from basal airway resistance). The compound under test was administered by i.v. bolus injection, and the subsequent peak inhibition of bronchoconstriction recorded.

The dose of compound required to reduce the U46619-induced bronchoconstriction by 50% is given as the BD$_{50}$. These results demonstrate in vivo antibronchoconstrictor activity.

| COMPOUND OF EXAMPLE | BD$_{50}$ ($\mu$mol/kg) |
| --- | --- |
| 1 | 3.6 |
| 2 | 6.5 |
| 3 | 3.8 |
| 4 | 5.3 |
| 5 | 1.0 |
| 7 | 3.6 |
| 8 | 1.5 |
| 9 | 4.5 |

Vasodilatation—In vivo

Male Wistar rats (300 g) were anaesthetised with a sodium 5-ethyl-5-(1-methylpropyl)-2-thiobarbiturate/-sodium pentobarbitone mixture i.p. (62.5 and 22.5 mg/kg respectively). The trachea was cannulated and the rats breathed spontaneously air enriched with O$_2$ (5 ml/min). Blood pressure was recorded from a carotid artery and a jugular vein was cannulated for the administration of compounds. The temperature of the animal was maintained at 37° C. by the use of an electric blanket. The abdominal aorta was separated from the inferior veno cava, distal to the renal arteries and was cannulated centrally to supply the perfusion pump with blood and distally for the perfusion of the hind quarters at constant pressure. The perfusion circuit was primed with 5% bovine serum albumin dissolved in 0.9% sodium chloride solution, pH adjusted to 7.4. Initially the pump rate was set between 10 and 15 ml/min to match the hind quarter perfusion pressure to that of the systemic circulation. Once set the pressure remained unaltered for the rest of the experiment. A change in the speed of the pump (equivalent to hindquarter blood flow) was used to assess the changes in hindquarter vascular resistance.

All compounds were administered as a bolus i.v. and from the dose response curves the dose required to produce a 50% increase in hindquarter blood flow (EDHQ$_{50}$) was determined in $\mu$moles/kg. The following results were obtained:

| COMPOUND OF EXAMPLE | EDHQ$_{50}$ ($\mu$mol/kg) |
| --- | --- |
| 1 | 10.8 |
| 5 | 3.7 |

Anti-allergic activity—in vitro

Male Hartley strain guinea pigs (weighing 250–300 g) were actively sensitized to ovalbumin (OA) by a modified Herxheimer method (J. Physiol. 117:251–258, 1952). The animals were injected intramuscularly with 0.7 ml of a 5.0% OA solution prepared in isotonic saline. Four weeks after sensitization tracheas were removed and cut into spiral strips. Each trachea was cut half, placed in 10-ml water-jacketed tissue baths and attached with biological tissue clips via silk suture to force displacement transducers for recording isometric tension. One half of each trachea served as a control for the corresponding drug-treated tissue. The tracheas were bathed in modified Krebs-Henseleit solution of the following composition (mM): NaCl, 118; KCl, 4.7; MgSO$_4$, 1.2; CaCl$_2$, 2.5; NaHCO$_3$, 25; KH$_2$PO$_4$, 1.2; and glucose, 10. The physiologic buffer was maintained at 37° C. and continually aerated with 95% O$_2$/5% CO$_2$. The tissue preparations were placed under 2 g passive tension and equilibrated for 60 minutes, during which time they were washed every 15 minutes with fresh buffer. Each tissue was pretreated for 45 minutes with meclofenamic acid (1 μM).

Tissues were pretreated with the compound under test (100 μM), or vehicle (0.4 mM NaOH) for 30 minutes prior to the addition of OA. OA (0.1 μg/ml) was added to all tissues and the contraction was monitored for 15 minutes. Previous experiments indicated that this concentration of OA produced the maximum antigen-induced contraction. At the conclusion of the experiment, a maximally-effective concentration of carbachol (10 μM) was added to each tissue and OA-induced responses were expressed as a percentage of this reference contraction. Since the compounds under test reduced basal tone, the absolute response (i.e., g tension) to carbachol was calculated as the difference between the tension after the addition of the test compounds and the maximum tension developed in the presence of carbachol. To evaluate effects of the test compounds, the degree of contraction was calculated 2 and 12 minutes after the addition of OA. OA-induced contraction of drug-treated tissues was expressed as a percentage of the response of vehicle-treated, paired controls.

When administered prior to OA challenge, both the compound of Example 1 (100 μM) and the compound of Example 5 (100 μM) significantly reduced basal tone. As a percentage of the maximum response to carbachol, the compound of Example 1 reduced basal tone by 17±3% and the compound of Example 5 by 24±7%. Administration of OA to vehicle-treated control tissues produced contractions which reached a maximum (67±2% of the maximum response to carbachol; N=4) within 3 minutes and were sustained over the 15-minute observation period. Two minutes after the addition of OA, the response of tissues treated for 30 minutes with the compound of Example 1 (100 μM) was 78±12% (N.S., P>0.05; N=4) of the control and the contractile response of those treated with the compound of Example 5 (100 μM) was 79±3% (P<0.05; N=4) of the control. Twelve minutes after OA challenge, contractile force had declined (P<0.05) in tissues treated with either the compound of Example 1 or the compound of Example 5 to 46±9% or 60±4%, respectively, of the control values.

Results are expressed as a mean ±S.E. of 4 experiments. Statistical significance of differences between the means of control and drug-treated groups was determined using a paired Student's t test.

These results indicate that compounds of Examples 1 and 5 inhibit antigen-induced contraction of the guinea-pig isolated trachea.

Anti-allergic activity—in vivo

Adult male albino Hartley strain guinea pigs weighing 400–600 g were actively sensitized to OA according to the procedure hereinbefore described. To measure pulmonary mechanics, a polyethylene catheter was inserted into the trachea of anesthetized (sodium pentobarbital, 35 mg/kg, i.p.) animals and airflow was measured via a heated pneumotachograph in combination with a differential pressure transducer connected to the pneumotachograph. Airflow and transpulmonary pressure signals were fed into an on-line pulmonary mechanics computer which integrated the flow signal to obtain tidal volume. Total pulmonary resistance ($R_L$) and dynamic lung compliance ($C_{DYN}$) were calculated at isovolumetric points according to the method of Amdur and Mead (Am. J. Physiol. 192:364–368, 1958).

A compound under test was dissolved in 25 mM NaHCO$_3$ plus one drop of polyethylene glycol 400 to a concentration of 100 mM. Based on the weight of the animal, the appropriate amount of solution was removed and the volume brought up to 1 ml with 25 mM NaHCO$_3$. For the intraduodenal administration of test compounds, a small midline incision was made in the abdomen, the duodenum was exposed, and a butterfly needle attached to plastic tubing was inserted. All solutions were adjusted to the same volume (1 ml) and administered through the butterfly needle and followed with 0.5 ml of distilled water. The needle was then removed and the abdominal incision was stapled to prevent heat loss.

Aerosols of OA were generated to deliver approximately 0.375 μl/breath. Pressure, flow rate and sensitivity were set such that a maximum pleural pressure of 20 cm water was attained during inhalation. One hour after the administration of the test compounds, quinea pigs were challenged with 5 inhalations of OA (0.5 mg/ml) via the tracheal cannula and changes in $C_{DYN}$ and $R_L$ were monitored for 10 minutes. Baseline values for $C_{DYN}$ and $R_L$ were 0.4–0.6 ml/cm water and 0.1–0.2 cm water/ml/sec, respectively.

Administration of OA to vehicle-treated, anesthetized guinea pigs produced bronchoconstriction which developed slowly over a 5-minutes period. Five minutes after OA challenge, $R_L$ had increased 162±40% and $C_{DYN}$ had decreased 51±26% (N=5). These changes in pulmonary function were stable over the remaining 5 minutes of the observation period. Intraduodenal administration of 100 μmol/kg of the compound of Example 1 (N=4) 60 minutes before OA challenge significantly reduced antigen-induced bronchoconstriction: 5 minutes after challenge, $C_{DYN}$ was unchanged from baseline (P<0.01 vs. vehicle-treated controls) and the increase in $R_L$ was limited to 51±26% (P<0.05 vs. vehicle-treated controls).

Results are expressed as a mean ± S.E. of 4 experiments. Statistical significance of differences between the means of control and drug-treated groups was determined using a unpaired Student's t test.

Inhibition of Phosphodiesterase (PDE)

Eight pig hearts/lungs were collected from the abattoir and kept on ice until the pulmonary arteries or aortas could be dissected and excess fat removed. 120 g of tissue was dissected. Unless otherwise stated all procedures were done at 4° C. Following dissection arteries were flash frozen in liquid nitrogen and stored at −70° C. until required. On the day of homogenisation, tissue was cooled with liquid nitrogen and broken into small pieces by striking with a hammer. The tissue was then homogenised in 15 mM BIS-TRIS, 1 μg/ml leupeptin and antipain, 2 μg/ml pepstatin A, 5 μM benzamidine, 2 mM EDTA (ethylenediaminetetraacetic acid) and 2 mM dithiothreitol, pH 6.5. Phenylmethanesulphonylfluoride (PMSF) was added to a final concentration of 50 μM just prior to homogenisation. The homogenate was then centrifuged for 20 minutes at 30,000 g. Supernatant was filtered firstly through glass wool and then a 0.45 μm filter. The resultant filtrate was then applied to a 60 ml DEAE-Sepharose® CL-6B (Diethylaminoethyl Cellulose with a bead size of 45-165 microns) (Pharmacia) column pre-equilibrated in homogenisation buffer. The column was washed with 150 mls of homogenisation buffer and PDE activities eluted with 150 ml of homogenisation buffer containing 100 mM sodium acetate. Six 25 ml fractions were collected, the flow rate throughout was 80 ml/hr.

Fractions 2 and 3 were pooled and BIS-TRIS, $MgCl_2$, $CaCl_2$ added to final concentrations of 50 mM, 7 mM and 5 mM respectively. PMSF, leupeptin, antipain and pepstatin A were also added at the concentrations described above for these components. The pH of this pooled sample was corrected to 6.9.

The sample was applied, at a flow rate of 3 ml/hr, to a tandem column set up. The first column in the tandem was a 5 ml calmodulin-agarose column (Sigma) and the second a 1.5 ml cibacron blue 3GA-agarose column (Sigma). Both columns were pre-equilibrated with 50 mM BIS-TRIS, 5 mM $MgCl_2$, 5 mM $CaCl_2$, 5 mM benzamidine, 2 mM dithiothreitol pH 6.9. Following application of the sample the columns were washed with 20 ml of equilibration buffer.

The cibacron blue-agarose column was then disconnected and washed with a variety of buffers as indicated below (Buffer A=50 mM BIS-TRIS, 5 mM benzamidine, 2 mM dithiotheitol pH 7.0).

20 ml Buffer A+2M NaCl, 5 mM $MgCl_2$
20 ml Buffer A+2M NaCl
20 ml Buffer A+2M NaCl, 10 mM EDTA PDE activity bound to the column was eluted with eight 2.5 ml aliquots of Buffer A containing 2M NaCl, 10 mM EDTA and 10 mM cGMP. Fractions found to contain PDE activity were pooled and concentrated to approximately ⅓ the original volume by dialysis for 2 hr against Buffer A:glycerol (50:50) containing 15 mM 2-mercaptoethanol, 2 mM EDTA. After dialysis the concentration of cGMP in the fraction was reduced by treatment using a PD-10 column (Pharmacia) using dialysis buffer.

The fraction produced was stored at −20° C. and for experiments diluted 50-fold and used as the source of PDE activity for the assay of compounds.

Properties of PDE activity

The PDE activity isolated by the procedure described above demonstrated considerable selectivity for cGMP as a substrate showing only poor rates of hydrolysis of cAMP. The PDE activity of this preparation could not be increased by the presence of $ca^{2+}$ (10 mM) and calmodulin (25 μg) in incubations and the hydrolysis of cAMP was not increased by the addition of 10 μM cGMP to incubations. The kinetic characteristics of this enzyme are summarised below.

$K_m$ cGMP = 1.3 μM
$K_m$ cAMP > 120 μM
Ratio of cGMP/cAMP hydrolysis at 1 μM substrate = 30.

Phosphodiesterase Assay

The assay was as described by Davis & Daly (1979) J. Cyclic Nucleotide Res., 5, 65-74, but with some modifications. The standard reaction mixture contained, in a final volume of 100 μl,
50 μM 5'-GMP (including 4000 dpm $^{14}$C-GMP)
1 μM 3', 5'-cGMP (including 0.1 μCi $^{3}$H-cGMP)
10 μM enzyme preparation
10 μM inhibitor dilution
and buffered with 50 mM TRIS/5 mM $MgCl_2$ pH 7.5. The reaction was initiated with enzyme, and was carried out at 37° C. for 5-10 minutes. The reaction was terminated by placing tubes in a boiling water bath for 2 minutes. 500 μM of 0.1M HEPES (N-2-hydroxyethylpiperazine-N'-2-ethanesulfonic acid) buffer pH 8.5 containing 0.1M NaCl was then added to each assay tube and the contents applied to Affigel 601 (Bio-Rad) boronate affinity chromatography media (1.2 ml bed volume) which had previously been equilibrated with 10 ml of HEPES/NaCl buffer. Unreacted $^3$H-cGMP was washed from the column with 10×1 ml HEPES/NaCl buffer. Labelled 5'-AMP was eluted into a scintillation vial with 6 ml 0.25M acetic acid and counted in a scintillation counter using 10 ml Instagel (Packard). Recoveries were between 50%-75% as measured by recovery of $^{14}$C-GMP. Assays were performed in duplicate and values corrected for blanks of <2%.

Calculation of $IC_{50}$ values $IC_{50}$ values (the concentration of inhibitor required for 50% inhibition of activity) were obtained by incubation of the enzyme at 1 μM cyclic GMP and a range of inhibitor concentrations.

| COMPOUND OF EXAMPLE | $IC_{50}$ (μM) |
| --- | --- |
| 1 | 0.96 |
| 2 | 4.49 |
| 3 | 5.04 |
| 4 | 1.74 |
| 5 | 1.25 |
| 7 | 5.26 |
| 8 | 6.79 |
| 9 | 3.64 |

EXAMPLE 1

2-(2-Propoxyphenyl)-6-purinone

A stirred mixture of 4,5-diamino-2-(2-propoxyphenyl)pyrimidin-6-one sulphate (1.5 g) (prepared by the addition of concentrated sulphuric acid to an ethanolic solution of the free base) and formamide (15 ml) was heated in an oil bath (temp. 190°-200° C.) for 70 minutes. When cool the mixture was filtered and the collected solid was washed with ethanol to give a crude product (1.1 g), m.p. 254°-259° C., which was recrystallised from ethanol to give the title compound, 0.72 g, m.p. 263°-265° C.

EXAMPLE 2

2-(2-Ethoxyphenyl)-6-purinone

In a similar manner to Example 1 reaction of 4,5-diamino-2-(2-ethoxyphenyl)pyrimidin-6-one sulphate (1.5 g) with formamide (15 ml) afforded the title compound, 0.36 g, m.p. 276°-277° C., (recrystallised from ethanol).

EXAMPLE 3

2-(2-Butoxyphenyl)-6-purinone

In a similar manner to Example 1 reaction of 4,5-diamino-2-(2-butoxyphenyl)pyrimidin-6-one sulphate (1.5 g) with formamide (5 ml) afforded the title compound, 0.65 g, m.p. 247°-248° C., (recrystallised from ethanol).

EXAMPLE 4

2-(2-Isobutoxyphenyl)-6-purinone

In a similar manner to Example 1 reaction of 4,5-diamino-2-(2-isobutoxyphenyl)pyrimidin-6-one sulphate (1.4 g) with formamide (5 ml) afforded the title compound, 0.24 g, m.p. 272°–273° C., (recrystallised from ethanol).

EXAMPLE 5

2-(2-Propoxyphenyl)purine-6,8-dione

A mixture of 4,5-diamino-2-(2-propoxyphenyl)-pyrimidin-6-one (1.3 g), and urea (1.5 g) was heated in an oil bath (temp. 190° C.) for 45 minutes. The resultant solid was digested with hot water, the mixture filtered and the solid washed with water to give a crude product, 1.36 g. Recrystallisation from dimethylformamide gave the title compound (1.01 g), m.p. >350° C., $\delta(DMSO-d_6)$, 1.01 (t, 3H); 1.88 (m, 2H); 4.09 (t, 2H); 7.10, 7.21, 7.52 and 7.76 (multiplets, 4H); ca 11.07, 11.55 and 11.95 (very broad singlets, 3H).

EXAMPLE 6

2-(2-Methoxyphenyl)purine-6,8-dione

In a similar manner to Example 5 reaction of 4,5-diamino-2-(2-methoxyphenyl)pyrimidin-6-one (0.93 g) with urea (1.20 g) afforded the title compound, 0.28 g, m.p. 329°–330° C. (recrystallised twice from dimethylformamide).

EXAMPLE 7

2-(2-Ethoxyphenyl)purine-6,8-dione

A solution of 4,5-diamino-2-(2-ethoxyphenyl)pyrimidin-6-one sulphate (2.0 g) in water (50 ml) was neutralized with ammonium hydroxide and extracted with chloroform. The organic extract was evaporated under reduced pressure to dryness and the residual free base was treated in a similar manner to Example 5 with urea (1.74 g) to afford after recrystallisation from dimethylformamide the title compound, 0.66 g, m.p. 349°–351° C.

EXAMPLE 8

2-(2-Butoxyphenyl)purine-6,8-dione

In a similar manner to Example 5 reaction of 4,5-diamino-2-(2-butoxyphenyl)pyrimidin-6-one (0.96 g) with urea (1.05 g) afforded the title compound, 0.26 g, m.p. 324°–326° C., (recrystallised from dimethylformamide).

EXAMPLE 9

2-(2-Isobutoxypheny)purine-6,8-dione

Carbonyldiimidazole (1.01 g) was added to 4,5-diamino-2-(2-isobutoxyphenyl)pyrimidin-6-one (1.50 g) in toluene (100 ml) and the resulting mixture was heated under reflux for one hour yielding a brown solid which was collected. This solid was washed with water and recrystallised from dimethylformamide to yield the title compound, 0.22 g, m.p. >360° C.

EXAMPLE 10

2-(2-Allyloxyphenyl)purine-6,8-dione 4,5-Diamino-2-(2-allyloxyphenyl)pyrimidin-6-one sulphate (0.8 g) was added to a stirred solution of carbonyldiimidazole (0.72 g) in dry pyridine (8 ml) under nitrogen. The resulting solution was stirred under nitrogen for 3 hours at ambient temperature and then the volume of the solution was reduced by evaporation under reduced pressure. The residual syrup was diluted with aqueous acetone (50%, 20 ml) and the resultant solid was collected, washed with water and acetone and dried to give a crude product (0.48 g). This material together with another crude sample (0.1 g, prepared in a similar manner as hereinbefore described) was recrystallised from acetic acid (ca 25 ml) by the addition of hot water (5 ml) to afford, after washing with acetic acid, water and ethanol and drying, the title compound, 0.4 g, m.p. 340°–345° C. dec., $\delta(DMSO-d_6)$, 4.68 (m, 2H); 5.2–5.4 (m, 2H); 5.9–6.2 (m, 1H); 7.07–7.2, 7.4–7.55, 7.6–7.7 (m's, 4H); 10.9, 11.45 and 12.1 (broad singlets, 3H).

EXAMPLE 11

2-(2-Propoxyphenyl)-6-purinone

A mixture of 4,5-diamino-2-(2-propoxyphenyl)-pyrimidin-6-one (0.3 g), formamidine acetate (0.18 g) and anhydrous sodium acetate (0.1 g) was heated in an oil bath at 155°–165° C. for 2½ hours. The mixture melted and then resolidified. Ethanol (1 ml) was added and the title compound was collected by filtration, 0.31 g, m.p. 256°–258° C.

EXAMPLE 12

2-(2-Propoxyphenyl)purine-6,8-dione

In a similar manner to Example 9 reaction of carbonyldiimidazole (4.98 g) with 4,5-diamino-2-(2-propoxyphenyl)pyrimidin-6-one (7.00 g) in toluene (350 ml) afforded the title compound, 3.76 g, m.p. >340° C. (recrystallised from dimethylformamide).

EXAMPLE 13

Pharmaceutical compositions for oral administration are prepared by combining the following:

|  | % w/w | | |
| --- | --- | --- | --- |
| 2-(2-Propoxyphenyl)-6-purinone | 0.5 | 3.0 | 7.14 |
| 2% w/w Soya lecithin in soya bean oil | 90.45 | 88.2 | 84.41 |
| Hydrogenated vegetable shortening and beeswax | 9.05 | 8.8 | 8.45 |

The formulations are then filled into individual soft gelatin capsules.

EXAMPLE 14

A pharmaceutical composition for parenteral administration is prepared by dissolving the title compound of Example 1 (0.02 g) in polyethylene glycol 300 (25 ml) with heating. This solution is then diluted with water for injections Ph. Eur. (to 100 ml). The solution is then sterilised by filtration through a 0.22 micron membrane filter and sealed in sterile containers.

What is claimed is:

1. A compound of the formula (1):

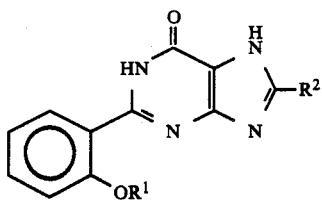

or a pharmaceutically acceptable salt thereof, wherein
$R^1$ is $C_{1-6}$alkyl or $C_{2-6}$alkenyl, and
$R^2$ is hydrogen or hydroxy.

2. A compound according to claim 1 wherein $R^2$ is hydrogen.

3. A compound according to claim 1 wherein $R^2$ is hydroxy.

4. A compound according to claim 1 wherein $R^1$ is $C_{2-5}$alkyl.

5. A compound according to claim 1 wherein $R^1$ is $C_{3-5}$alkenyl.

6. A compound according to claim 1 which is: 2-(2-ethoxyphenyl)-6-purinone or a pharmaceutically acceptable salt thereof.

7. A compound according to claim 1 which is: 2-(2-butoxyphenyl)-6-purinone or a pharmaceutically acceptable salt thereof.

8. A compound according to claim 1 which is: 2-(2-isobutoxyphenyl)-6-purinone or a pharmaceutically acceptable salt thereof.

9. A compound according to claim 1 which is: 2-(2-methoxyphenyl)purine-6,8-dione or a pharmaceutically acceptable salt thereof.

10. A compound according to claim 1 which is: 2-(2-ethoxyphenyl)purine-6,8-dione or a pharmaceutically acceptable salt thereof.

11. A compound according to claim 1 which is: 2-(2-butoxyphenyl)purine-6,8-dione or a pharmaceutically acceptable salt thereof.

12. A compound according to claim 1 which is: 2-(2-isobutoxypheny)purine-6,8-dione or a pharmaceutically acceptable salt thereof.

13. A compound according to claim 1 which is: 2-(2-allyloxyphenyl)purine-6,8-dione or a pharmaceutically acceptable salt thereof.

14. 2-(2-Propoxyphenyl)-6-purinone or a pharmaceutically acceptable salt thereof.

15. 2-(2-Propoxyphenyl)purine-6,8-dione or a pharmaceutically acceptable salt thereof.

16. A pharmaceutical composition for effecting bronchodilatation which comprises an effective amount of a compound according to claim 1 and a pharmaceutically acceptable carrier.

17. A pharmaceutical composition for effecting vasodilatation which comprises an effective amount of a compound according to claim 1 and a pharmaceutially acceptable carrier.

18. A pharmaceutical composition for effecting inhibition of a calmodulin insensitive cyclic GMP of phosphodiesterase which comprises an effective amount a compound according to claim 1 and a pharmaceutically acceptable carrier.

19. A method for effecting bronchodilatation in a host in need thereof by administration of a non-toxic but effective amount of a compound according to claim 1.

20. A method for effecting vasodilatation in a host in need thereof by administration of a non-toxic but effective amount of a compound according to claim 1.

21. A method for effecting inhibition of a calmodulin insensitive cyclic GMP phosphodiesterase in a host in need thereof by administration of a non-toxic but effective amount of a compound according to claim 1.

* * * * *